United States Patent [19]

Mathieu et al.

[11] Patent Number: 5,015,374

[45] Date of Patent: May 14, 1991

[54] CLOSURE CAP FOR DIALYZERS

[75] Inventors: Bernd Mathieu, Spiesen-Elversberg; Michael Rinck, St. Ingbert-Hassel; Jürgen Schnur, Oberthal; Dieter Selzer, Namborn; Wolfram Weber, Spiesen-Elversberg, all of Fed. Rep. of Germany

[73] Assignee: Fresenius AG, Bad Homburg, Fed. Rep. of Germany

[21] Appl. No.: 386,284

[22] Filed: Jul. 27, 1989

[30] Foreign Application Priority Data

Jul. 28, 1988 [DE] Fed. Rep. of Germany ....... 3825573

[51] Int. Cl.⁵ .................... B01D 63/00; B01D 65/02
[52] U.S. Cl. ......................... 210/232; 210/321.69; 210/321.72; 210/541; 285/319; 285/921
[58] Field of Search ............. 210/232, 321.71, 321.72, 210/321.73, 321.74, 321.75, 321.76, 321.77, 321.78, 321.79, 321.8, 321.81, 541, 321.69; 285/319, 320, 396, 399, 403, 417, 901, 921

[56] References Cited

U.S. PATENT DOCUMENTS

| 4,266,814 | 5/1981 | Gallagher | 285/319 |
| 4,673,506 | 6/1987 | Henne et al. | 210/636 |
| 4,707,335 | 11/1987 | Fentress et al. | 210/321.71 |
| 4,781,400 | 11/1988 | Cunningham | 285/921 |

Primary Examiner—W. Gary Jones
Attorney, Agent, or Firm—Marshall, O'Toole, Gerstein, Murray & Bicknell

[57] ABSTRACT

The invention relates to a closure cap (1) for dialyzers which is suitable for a so-called in-line sterilization. For this purpose the closure cap (1) comprises two cap parts (2, 3) of which the first cap part (2) is adapted to be mounted on a dialyzer flange (4) while the second cap part (3) is arranged movably in a receiving compartment (5) of the first cap part (2) between an open position and a closure position. In an open position passage of a sterilization medium is possible so that all the parts, sealing and guide surfaces can be reliably sterilized. In the closure position the second cap part (3) is pushed into a sealing position within the first cap part (2) so that contamination of the dialyzer after removal from the sterilization apparatus can be prevented with certainty.

37 Claims, 4 Drawing Sheets

CLOSURE CAP FOR DIALYZERS

DESCRIPTION

The invention relates to a closure cap for dialyzers according to the preamble of claim 1 and a dialyzer provided with such a closure cap.

After their actual manufacture dialyzers must be sterilized before they are stored. In devising the sterilization method as so-called in-line method any open contact with the external air after carrying out the sterilization step must be avoided. For this reason, the dialyzer must be sealed in germ-tight manner before it is removed from the sterilization bench.

A closure cap corresponding to the preamble of claim 1 comprises a first cap part which is introduced with two legs into an annular recess of a dialyzer flange and to which a second cap part is secured which is movable between an open and a closure position. Said second cap part comprises a closure plate which is connected via an articulate connection to the first cap part and on which a guide member is provided which in the closure position engages into a connecting flange of the first cap part.

It has however been found that the closure cap according to the preamble is not germ-tight enough.

Furthermore, the known closure cap does not make it possible during the sterilization to sterilize the flange inner surfaces by the sterilizing agent as well. Finally, the closure cap according to the preamble is disadvantageous in so far as it is not suitable for use in in-line sterilization methods for dialyzers.

The problem underlying the present invention is therefore to provide a closure cap for dialyzers according to the preamble of claim 1 which is suitable for use in in-line sterilization methods for dialyzers, which permits a germ-tight closure both on the blood side and on the dialyzate side and which moreover permits the simultaneous sterilization of the flange inner surfaces in the course of the sterilization.

This problem is solved by the features of claim 1.

The closure cap according to the invention permits a germ-tight sterile closure when the closure cap is fitted and in the closure position which permits insertion of the externally unsterile dialyzers into an unsterile surrounding packing. In a first embodiment a covering is effected in which the outer sleeve engages over the dialyzer flow in sterile manner externally whilst in a second embodiment the sterile seal is via an elastic sealing means.

Due to the design-inherent connection facility to an in-line sterilization apparatus it is possible to avoid LF-protected aseptic closure stations.

Furthermore, the sterilization of the flange inner sides of the dialyzer increases the microbiological safety.

The in-line sterilizable closure cap according to the present invention is advantageously suitable for preassembly in the opened state and remains on the dialyzer during and after the sterilization. All the cap inner sides are also sterilized and it is possible to automatically seal the closure cap before removal of the dialyzer from the production process so that a germ-tight seal is ensured both on the blood side and on the dialyzate side.

This avoids any open contact with the outer air after carrying out the sterilization so that the dialyzer is sealed from the outside in germ-proof manner; in addition to automatic locking, manual locking is also possible.

By using the closure cap according to the invention, to avoid transmission of contaminations it is possible to keep completely germ-free a connection means provided on the dialyzer flange, for example in the form of a screw connection.

Due to the design of the closure cap according to the invention it is advantageously possible to sterilize all the sliding surfaces and the contact region to the dialyzer flange, the sterilization of the connector extension on the flange also being possible.

A further advantage to be emphasized of the closure cap according to the invention is that it is suitable for all types of sterilization methods with all sterilization agents usual at present, such as hot and cold sterilization media. Furthermore, the closure cap according to the invention can be used both in dialyzers which are dried after the sterilization and in dialyzers which are filled for example with brine solution.

Moreover, the closure cap according to the invention can be used both on the blood side of the dialyzer and on the dialyzate side thereof.

The subsidiary claims contain advantageous further developments of the invention. In particular, it is possible to design the arresting means as intactness fastener or sealing means which can be provided with exactly defined desired breakage points.

All in all, the construction of the closure cap according to the invention makes it possible to carry out in-line sterilization methods with liquid and gaseous/vapour media and the dialyzers can be delivered both filled with solution and dry.

Further details, features and advantages of the invention will be apparent from the following description of examples of embodiment with the aid of the drawings, wherein.

Figure 1:
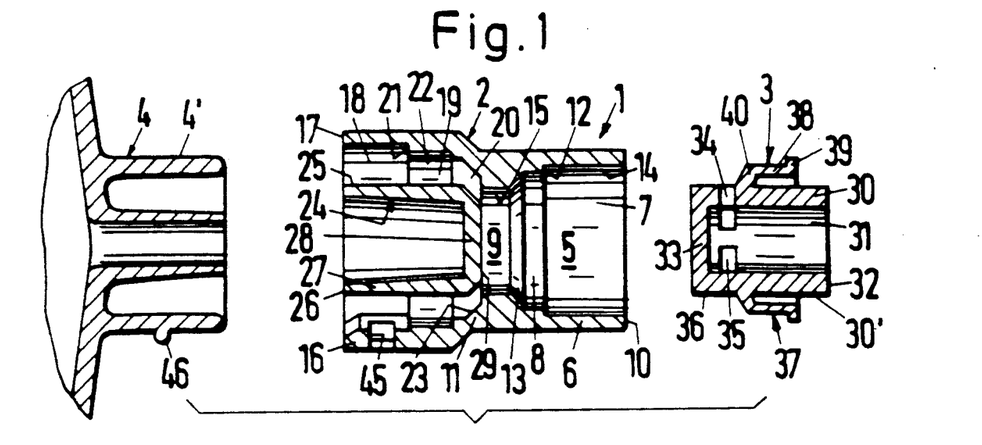
FIG. 1 is a sectioned exploded illustration of the closure cap according to the invention prior to assembly on the dialyzer flange.
Figure 2:
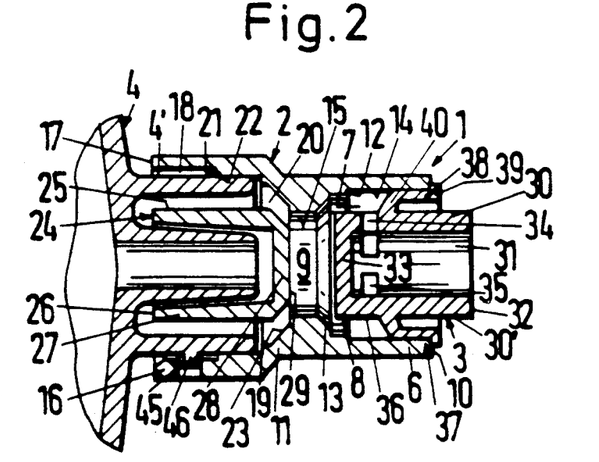
FIG. 2 is a sectioned view of the closure cap of FIG. 1 in the open position and in the state mounted on the dialyzer.
Figure 3:
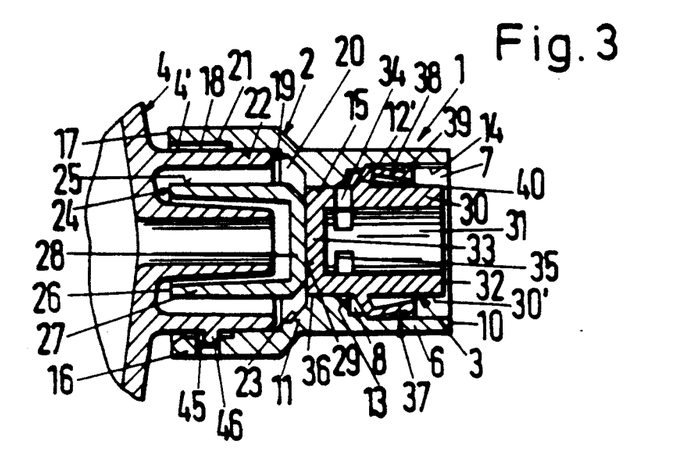
FIG. 3 is a view of the closure cap corresponding to FIG. 2 but in the closed position.

In FIGS. 1 to 3 a closure cap 1 according to the invention for the blood side of dialyzers is illustrated.

The closure cap 1 comprises a first cap part 2 a second stopper-like cap part 3.

The first cap part 2 is made substantially tubular, a preferred embodiment being cylindrical. Furthermore, the first cap part comprises a first portion 6 and a second portion 16. In the first portion 6, the outer dimension of which is less than that of the second portion 16, a receiving compartment 5 for the second cap part 3 is arranged. Furthermore, the first portion 6 forms a rearward portion of the first cap part 2 which forms the connection point to an in-line sterilization apparatus and for this purpose can be provided if necessary with suitable connection means.

The receiving compartment 5 comprises three consecutive subchambers 7, 8, 9. Said subchambers 7, 8, 9 are arranged from an open end side 10 with decreasing diameters towards an end region 11 of the first portion 6 opposite the end side 10 in said portion 6. Between the first subchamber 7, which adjoins the end side 10 and has the largest diameter or the largest internal dimension, and the second subchamber 8 a step 12 is arranged which extends inwardly substantially perpendicularly to the longitudinal axis of the first cap part 2.

The second subchamber 8 and the third subchamber 9, which has the smallest internal diameter and the smallest internal dimension, are connected together via a frustoconical intermediate portion 13 whose inner surface provides a gradual transition from the inner surface of the second subchamber 8 to the inner surface 15 of the third subchamber 9.

The inner surface 14 of the first subchamber 7 is made smooth and serves as guide and retaining surface for the second cap part 3 which will be described in detail hereinafter. The inner surface 15 of the third subchamber 9 likewise forms a guide surface for a corresponding surface of the cap part 3, as will also be explained in detail hereinafter.

The second portion 16 of the first cap part 2 is connected to the first portion 6, the second portion 16 adjoining an end region 11 of the first portion 6 via a frustoconical connecting surface. The second portion 16 is open at its end side 17 opposite the end face 10, the end side 17 being adjoined inwardly by three subspaces 18, 19 and 20. The subspace 18 directly adjoining the end side 17 has a greater internal diameter or a greater clear width than the middle subspace 19. The subspaces 18 and 19 are connected together via a step 21 which extends inwardly substantially perpendicularly to the longitudinal axis of the first cap part 2.

As apparent from FIG. 2 the inner surface 22 of the second subspace 19 forms a guide and sealing surface for a dialyzer flange 4. The inner surface 22 of the second subspace 19 lies on the correspondingly outwardly directed wall region 4' of an outer encircling connector extension. As a result, the inner space defined by the dialyzer flange 4 and the subspaces 18 to 20 is sealed.

The third subspace 20 of the second portion 16 comprises a frustoconical inner surface 23 which provides a gradual transition between the second subspace 19 and the third subspace 9 of the first portion 6. As apparent from FIG. 1, this arrangement provides a flow connection which extends through the entire inner space of the first cap part 2 from the one end side 10 to the other end side 17.

As further apparent from FIG. 1, within the subspaces 18 to 20 concentrically to the second portion 16 a pot-shaped insert member 24 is fixed, for example by radially outwardly directed struts. The outer surface 25 of the insert member 24 defines a free flow passage with the inner surfaces of the subspaces 18 to 20.

In particular, the insert member 24 comprises an open end side 26 which preferably lies in a plane with the open end side 17 of the second portion 16. It is however conceivable for the end sides 26 and 17 to be arranged in different planes.

The insert member 24 further comprises a preferably cylindrical boundary wall 27 which extends concentrically round the longitudinal axis of the first cap part 2. At the side opposite the open end side 26 said boundary wall 27 is preferably integrally connected to a closure or termination wall 28 which extends perpendicularly to the longitudinal axis of the first cap part 2. The closure wall 28 comprises on its side facing the subchamber 9 an outer surface 29 which is likewise preferably arranged perpendicularly to the longitudinal axis of the cap part 2.

As further apparent from FIG. 1, in the wall of the second portion 16 a recess 45 is disposed which passes through the wall. Said recess or cutout 45 serves to fix the second cap part 2 on the dialyzer flange 4 which for this purpose comprises a detent projection 46 which in the embodiment illustrated projects radially outwardly. The detent position can be seen in detail in FIGS. 2 and 3. To assume this detent position the corresponding portions of the dialyzer flange 4 and of the second cap part 2 are made elastically yielding and provided with corresponding runup ramps which can be seen in detail in the illustration of FIG. 1. Instead of such a snap-action detent connection it is also possible to provide a threaded connection, a bayonet fastener or similar locking means.

Also shown in detail in FIG. 1 is the form of the second cap part 3. The second cap part 3 is made pot-shaped and for this purpose comprises a wall 30 which extends round the longitudinal axis and defines an inner space 31. The wall 30 is preferably made cylindrical. The inner space 31 is open at an end face 32 and the rear portion 30' of the wall there can if necessary form the connecting portion for the in-line sterilization apparatus. Said portion can be provided with suitable connection means. At the opposite end side the inner space 31 is closed by a closure wall 33 arranged substantially perpendicularly to the longitudinal axis.

In the case of the example the wall 30 comprises two connecting openings 34 and 35 which extend from the inner space 31 up to the outer wall surface 36 of the wall 30 so that they create a flow formation from the outer region of the second cap part 3 to its inner space 31.

Furthermore, FIG. 1 shows the arrangement of a guide and retaining means 37 on the outer wall surface 36 of the wall 30. In the case of the example the guide and retaining means 37 comprises a guide ring 38 which extends concentrically at a certain spacing round the outer wall surface 36. The guide ring 38 is provided at its end facing the end side 32 with a stop ring 39 which extends radially outwardly from the guide ring 38 and thus forms an outwardly projecting edge. At its other end the guide ring 38 is connected via a collar 40, arranged inclined with respect to the longitudinal axis, to the wall 30. Preferably, this arrangement is an integral connection.

The closure cap 1 described above is shown in FIG. 2 in its open position. In this position the second cap part 3 has been inserted into the receiving compartment 5 of the first cap part 2. As shown in FIG. 2, in this position the outer surface of the guide ring 38 bears on the inner surface 14 of the first subchamber 7. Furthermore, the stop ring 39 of the guide ring 38 bears on the end face of the end side 10 of the first cap part 2 and thus limits the axial position of the second cap part 3 within the receiving compartment 5 of the first cap part 2. In the position shown in FIG. 2 the first cap part 2 is connected to the dialyzer flange 4 in the manner described above, the sealing surfaces 4' and 22 sealing the space formed between the dialyzer flange and the second portion 16 of the first cap part 2.

As FIG. 2 further illustrates, by the axially limited position of the second cap part 3 within the receiving compartment 5 a free passage of the sterilization medium through the entire arrangement is ensured. Consequently, it is possible in the sterilization to completely sterilize all the parts and sliding surfaces of the arrangement shown in FIG. 2 and thus render them completely free from germs. This makes it possible to use the closure cap according to the invention in a so-called in-line sterilization, which means that the sterilization takes place in the production line of the dialyzer.

After completion of the sterilization the second cap part 3 is moved, preferably automatically, into its closure position shown in FIG. 3. For this purpose the second cap part 3 is pressed along the longitudinal axis in the direction towards the insert member 24. FIG. 3 shows that in this movement the elastically resilient guide ring 38 deforms towards the wall 30 so that insertion of the second cap part 3 into the receiving compartment 5 is possible. The insertion is continued until the outer surface of the closure wall 33 of the second cap part 3 comes into sealing engagement with the outer surface 29 of the insert member 24. The inner surface 15 of the third subchamber 9 here takes on a guiding and sealing function. The closure or sealing position of the second cap part 3 within the first cap part 2 illustrated in FIG. 3 is secured by the engagement of the stop ring 39 on the inner surface 14 because the guide ring 38 due to its elastically resilient construction presses the stop ring 39 against the inner surface 14. It is possible to design the aforementioned parts in such a manner that the second cap part 3 forming a plug can no longer be moved into its open position. In this position the dialyzer, which due to the closure cap 1 is sealed germ-free, can be removed from the sterilization apparatus and by the arresting means constructed as bayonet, snap-action or screw connection, a detaching of the closure cap 1 from the sterilizer, for example in the unsterile packaging, is reliably prevented.

As already mentioned, the closure cap 1 illustrated in FIGS. 1 to 3 is the embodiment for the blood side of the dialyzer.

Figure 4:
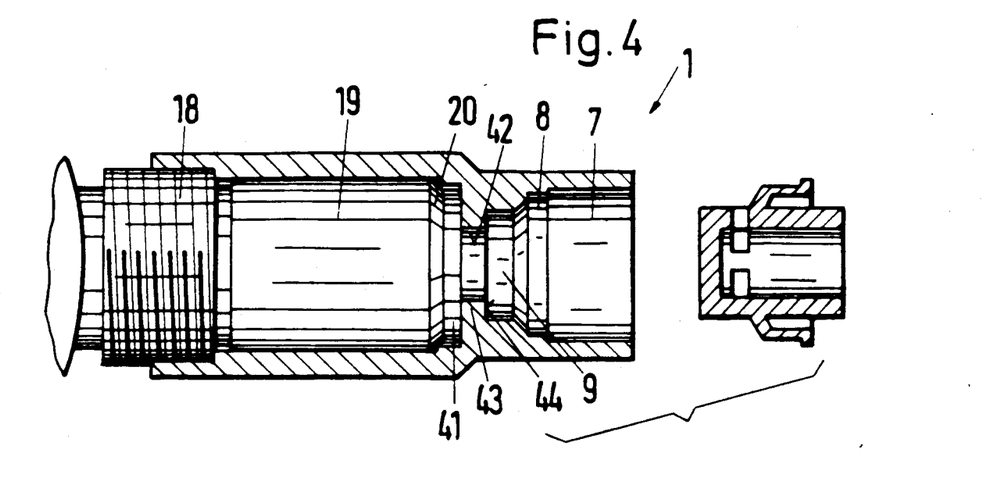
FIG. 4 is a view of an embodiment of the closure cap corresponding to FIG. 1 provided for use on the dialyzate side.
Figure 5:
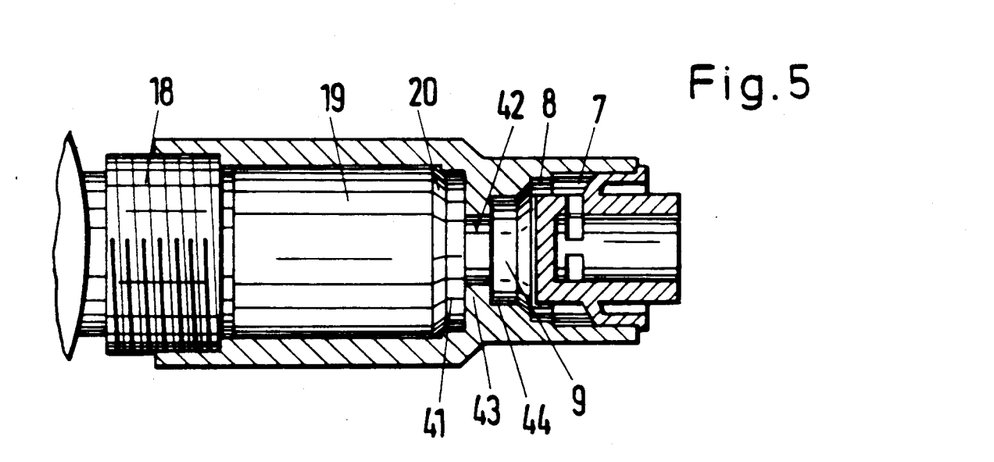
FIG. 5 is a view of the closure cap according to FIG. 4 corresponding to FIG. 2.
Figure 6:
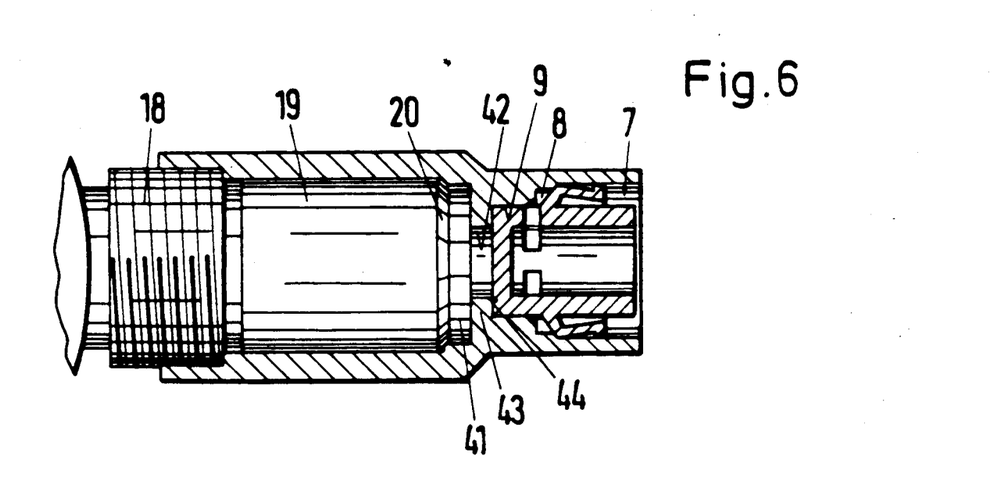
FIG. 6 is a view of the closure cap according to FIGS. 4 and 5 corresponding to FIG. 3.

On the other hand, in FIGS. 4 to 6 the embodiment of the closure cap 1 according to the invention for the dialyzate side is shown. As apparent from FIGS. 4 to 6 the closure cap for the dialyzate side is constructed in its essential parts exactly like the closure cap 1 for the blood side. In this respect reference can therefore be made to the explanations on FIGS. 1 to 3.

As difference for adaptation to the dialyzate side of the dialyzer it is first to be pointed out that the third subspace 20 of the second portion 16 forms a transition between the second subspace 19 and the fourth subspace 41 which via a central connecting recess 42 is connected to the third subchamber 9 of the first portion 6. The connecting recess 42 is defined by an encircling stop wall 43 projecting inwardly to the longitudinal axis. The stop wall 43 comprises a sealing surface 44 which is arranged on a side facing the third subchamber 9.

It is additionally apparent from FIG. 4 that the second subspace 19 is made longer in the axial direction than the second subspace 19 of the first cap part 2 according to FIGS. 1 to 3. FIGS. 4 to 6 also show that the first cap part 2 in this embodiment is connected via a screw connection to the corresponding connector piece of the dialyzate side. This is however not an essential difference because the snap-action detent connection shown in FIGS. 1 to 3 may also be provided.

FIGS. 5 and 6 again show the open and closure position of the closure cap 1. These positions correspond essentially likewise to the positions according to FIGS. 3 and 4. However, due to the differently constructed first cap part 2, which does not have an insert member, the sealing point is located between the sealing surface 44 of the stop wall 43 and the corresponding adjacent surface region of the closure wall 33 of the second cap part 3. This is apparent in detail from the illustration of FIG. 6.

Otherwise, with the embodiment f the closure cap 1 according to the invention for the dialyzate side the same effects and advantages are achieved as those of the closure cap construction for the blood side so that in this respect as well attention may be drawn to the corresponding explanations in connection with FIGS. 1 to 3.

It should be additionally pointed out regarding the cooperating arresting means 45 and 46 on the first cap part 2 and on the dialyzer flange 4 respectively that the latter may be designed as intactness seal closure. It is conceivable for this purpose to provide a tear-off securing means or to provide the arresting means 46 constructed as nose on the dialyzer flange 4 with an exactly defined desired breakage point.

Finally, the closure cap 1 can also be made in one piece provided that corresponding injection-molding technology precautions are taken. Accordingly, the two cap parts 2 and 3 may be connected together via a flexible web which allows both an axial pushing together of the two parts as well as a radial turning of said two parts to a certain extent. This web, not shown, is integrally formed on the two cap parts.

Figures 7, 9, 11:
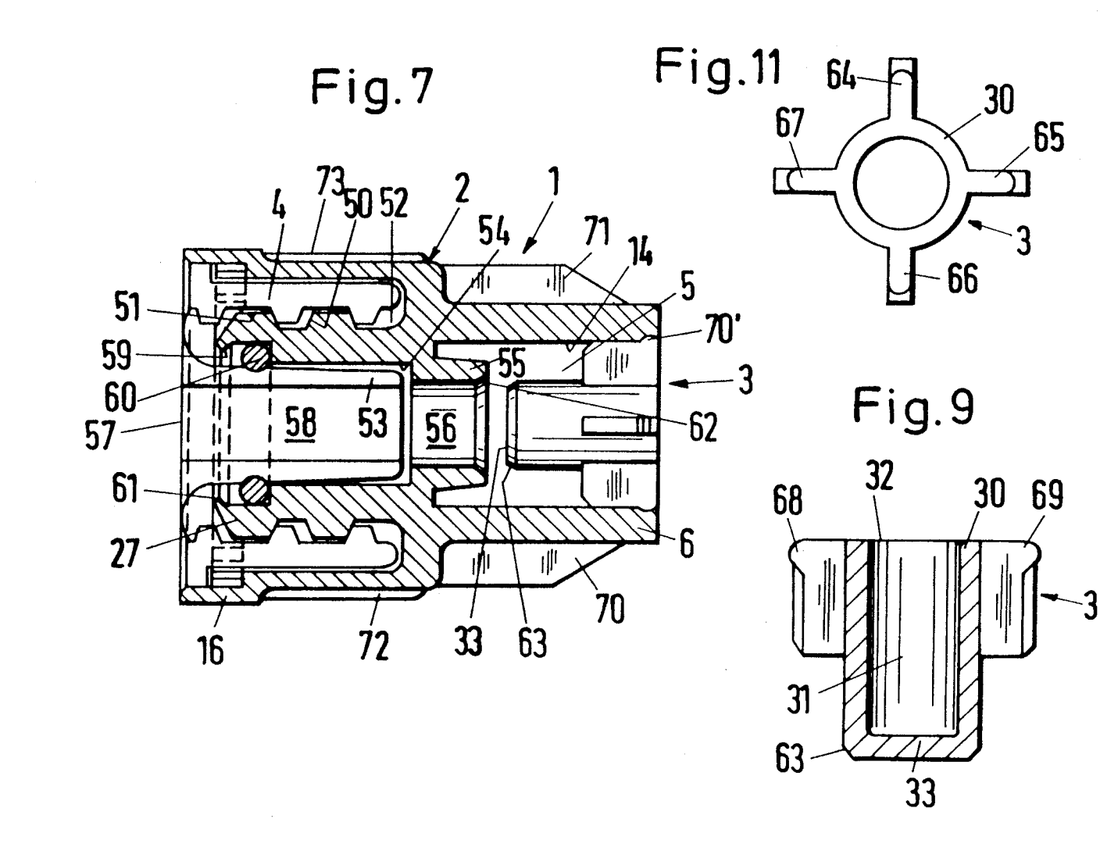
FIG. 7 is a view of a second embodiment of a closure cap corresponding to FIG. 2 for the blood side of dialyzers.
FIG. 9 is a longitudinal section through a stopper-like cap part of the second embodiment.
FIG. 11 is an end view of the cap part according to FIGS. 9 and 10.

In accordance with FIG. 7 a second embodiment of a closure cap according to the invention is shown, for the blood side of dialyzers, all the parts identical with the previous embodiment being provided with the same reference numerals.

Accordingly, the second embodiment of the closure cap 1 also comprises a first cap part 2 and a second stopper-like cap part 3.

The first cap part 2 is again made essentially tubular, cylindrical in a particularly preferred embodiment. As FIG. 7 shows the cylindrical boundary wall 27 of the cap part 2 of the second embodiment is provided with an outer thread 50 which in the assembled state cooperates with an inner thread 51 of the only partially illustrated dialyzer flange 4. The outer dialyzer flange 4 is accommodated in an elongated receiving compartment 53 which is arranged between the outer second cylindrical portion 16 and the inner boundary wall 27.

An inner cylindrical dialyzer collar 53 arranged concentrically with the outer dialyzer flange 4 is arranged in a concentrically disposed receiving recess 54 of the portion 16 and extends into the region of a cylindrical extension 55 which is provided with a passage recess 56 which is in communication with the recess 54 of the second portion 16.

Facing towards the open end side 57 the boundary wall 27 comprises an annular encircling groove 59 in which a sealing element, preferably in the form of an O ring 60, is inserted. As FIG. 7 shows the O ring in the assembled state bears on the dialyzer collar 53 and the boundary walls of the groove 59 in such a manner that in the embodiment according to FIG. 7 at this point a sterile sealing of the dialyzer is effected when the closure cap 1 is screwed on. FIG. 7 shows that here on the side of the open end side 57 the groove 59 is provided with an encircling inwardly directed collar 61 which serves to prevent the O ring 60 slipping out of the groove 59 in the unassembled state of the closure cap 1.

As further shown in FIG. 7 a flow connection is established between a flow passage 58, which is arranged within the dialyzer collar or the inner dialyzer flange 53, and the passage recesses 56 of the extension 55. The passage recess 56 of the extension 55, in the position of the plug-like cap part 3 shown in FIG. 7, again communicates with the receiving compartment of the first portion 6 of the first cap part 2 because the plug-like cap part 3 in the position illustrated in FIG. 7 is arranged at the end sides in the receiving chamber 5 so that the closure wall 33 of the second cap part 3 is spaced from an annular sealing surface 62 which is chamfered in frustoconical manner. A correspondingly formed outer sealing surface 63 is arranged on the outer edge of the closure wall 33.

Figure 10:
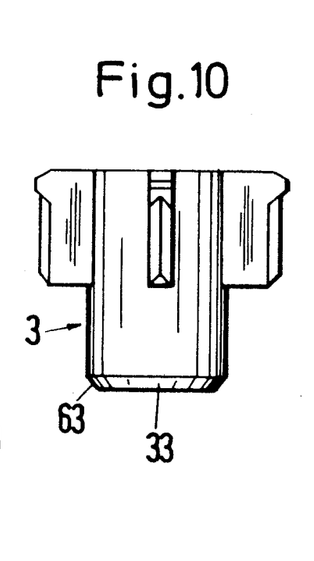
FIG. 10 is an end view of the cap part according to FIG. 9

The cap part 3 is guided within the receiving recess 5 via for example a total of four vanes 64 to 67, the arrangement and configuration of which can be seen in particular from FIGS. 9 to 11. The vanes or fins 64 to 67 are made flat and extend from the end side 32 of the cap part 3 approximately into the centre portion thereof, seen in the longitudinal direction. As FIG. 11 shows the vanes 64 to 67 are each spaced by 90° and arranged round the outer periphery of the cap part 3 and have at their radially outer ends on the side of the end side 32 projections of which the projections 68 and 69 are visible in FIGS. 9 and 10. At the end side the first portion 6 of the cap part 2 is provided with an outwardly widening chamfer 70, the form of which corresponds to the projections of the vanes 64 to 67.

In the control position illustrated in FIG. 7 the projections of the vanes 64 to 67 lie in said chamfer 70 so that a certain resistance must be overcome on pressing the second cap part 3 in the direction towards the extension 55. By the radially outwardly extending arrangement of the vanes 64 to 67 the second cap part 3 is centered in the receiving compartment 5 and can be pushed from the position illustrated in FIG. 7 into a position into the inner space in which sealing surfaces 62 and 63 bear on each other, thereby providing a sealing of the through recess 56 so that the dialyzer is hermetically sealed. On moving back to the position shown in FIG. 7 the flow connection between the passage recess 56 and the receiving compartment 5 is reestablished and due to the arrangement of the vanes 64 to 67 at intervals of 90° on the outer periphery of the cap part 3 between the vanes and the inner boundary wall 14 a flow cross-section is likewise freed.

With regard to the embodiment of the cap part 2 of the closure cap 1 according to FIG. 7 it should further be stated that said cap comprises on the first and second portions 6 and 16 respectively in each case a plurality of outwardly directed reinforcing ribs of which the reinforcing ribs 70 to 73 are visible in FIG. 7. The reinforcing ribs 70 and 71 on the first portion 6 are drawn radially outwardly to such an extent that they correspond approximately to the outer diameter of the second portion 16. Between the ribs 70 and 71 a plurality of further ribs with radially smaller dimensions may be provided.

Otherwise, with regard to all identical features of the embodiments according to FIGS. 1 to 3 and those according to FIGS. 7 to 11 attention is drawn to the above explanations.

Figure 8:
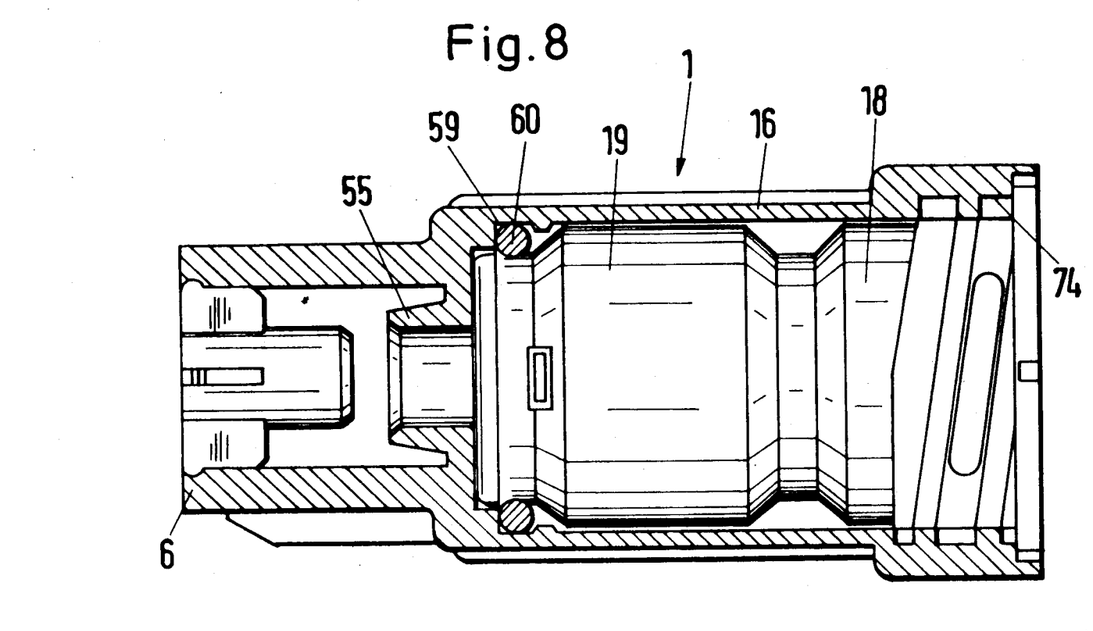
FIG. 8 is a view corresponding to FIG. 5 of the second embodiment of a closure cap for the dialyzate side.

Finally, FIG. 8 shows a cap part 1 for the dialyzate side which in its essential features corresponds to the cap part according to the embodiment of FIG. 7. Consequently, here as well a sealing is provided by means of an elastic sealing device, preferably in the form of an O ring 60, and a second cap part 3 is used which corresponds to that of FIGS. 9 to 11. Consequently, in this respect reference can be made to the explanations of FIGS. 7 and 9 to 11.

Due to the different configuration of the dialyzate-side flange of the dialyzer the cap part 1 on the dialyzate side is formed corresponding to the constructional modifications according to the embodiment of FIGS. 4 to 6 and thus comprises in particular an extended second portion 16 which adjoins the first portion and in the region of the end-side opening of which an inner thread 74 is arranged for cooperating with an outer thread on the dialyzate-side flange of the dialyzer. Furthermore, as difference from the cap part according to FIG. 7 it should be emphasized that the O ring 60 is arranged nearer the extension 55 but also lies in a groove 59 so that when the dialyzate-side cap part 1 illustrated in its open position in FIG. 8 is screwed on a sterile seal likewise results due to the O-ring seal 60.

With regard to all other common features attention can again be drawn to the embodiment according to FIGS. 4 and 6 and to the features in common with the cap part 1 according to FIG. 7.

What is claimed is:

1. In a closure cap for dialyzers comprising first and second cap parts (2, 3), of which the first cap part (2) comprises means for attaching the first cap part to a dialyzer flange (4) while the second cap part (3) is movable between an open position in which the passage of a sterilization medium takes place and a closure position, the improvement wherein:
   the first cap part (2) comprises a connection portion (16) having means (22, 60) for sealing the dialyzer flange (4) in the assembled state in a sterile manner and a first portion (6) which is adapted to be brought into flow connection with an in-line sterilization means.

2. The improvement according to claim 1, characterized in that the first cap part (2) is made substantially tubular and comprises at one side a receiving compartment (5) for the second cap part (3) which is arranged in the first portion (6).

3. The improvement according to claim 2, characterized in that the receiving compartment (5) comprises first, second and third consecutive subchambers (7, 8, 9) which are arranged from an open end side (10) with decreasing diameters up to an end region (11) of the first portion (6) opposite the end side (10) in said portion.

4. The improvement according to claim 3, characterized in that between the first subchamber (7) with the greatest diameter and the second subchamber (8) a step (12) extending inwardly substantially perpendicularly to the longitudinal axis of the first cap part (2) is arranged.

5. The improvement according to claim 3, characterized in that the second subchamber (8) and the third subchamber (9) of smallest diameter are connected together via a conical intermediate portion (13).

6. The improvement according to claim 3, characterized in that an inner surface (14) of the fist subchamber (7) forms a guide and retaining surface for the second cap part (3).

7. The improvement according to claim 3, characterized in that an inner surface (15) of the third subchamber (9) also forms a guide surface for the second cap part (3).

8. The improvement according to claim 2, characterized in that the first cap part (2) comprises an elastic sealing means (60).

9. The improvement according to claim 8, characterized in that the elastic sealing means is formed as O ring (60) which is arranged in an annularly encircling inner sealing groove (59) and in the assembled state cooperates with a dialyzer collar (53) of the dialyzer flange (4) for generating the sealing effect.

10. The improvement according to claim 8, characterized in that in the receiving compartment (5) a cylindrical extension (55) is arranged which comprises an inner passage recess (56) which is in flow connection with the receiving compartment (5) in the open position of the cap part (3).

11. The improvement according to claim 10, characterized in that the extension (55) comprises an annular sealing surface (62) which cooperates with a complementarily formed annular sealing surface (63) of the second cap part (3) in the closure position thereof.

12. The improvement according to claim 8 characterized in that the second cap part (3) comprises four vanes (64 to 67) which are arranged at an angle of 90° and disposed circumferentially on an outer wall (30) of the cap part (3).

13. The improvement according to claim 12, characterized in that the vanes (64 to 67) are provided with projections (68, 69) which project radially outwardly from outer edges of the vanes (64 to 67).

14. The improvement according to claim 8, characterized in that the closure cap (1) usable on a blood side of a dialyzer and is provided with an outer thread (50) arranged in a receiving compartment (52) for cooperating with an inner thread (51) of the dialyzer flange (4).

15. The improvement according to any one of claims 8 to 14, characterized in that the closure cap (1) is usable on a dialyzate side of a dialyzer and provided with an inner thread (74) for cooperating with an outer thread on the dialyzer flange.

16. The improvement according to claim 1, characterized in that the connection portion (16) is connected to the first portion (6) following an end region (11) thereof and its outer diameter is greater than the outer diameter of the first portion (6).

17. The improvement according to claim 16, characterized in that the connection portion (16) has an opened end side (17) adjoined inwardly by first, second and third subspaces (18, 19, 20).

18. The improvement according to claim 17, characterized in that the first subspace (18) immediately adjoins the end side (17) and has a greater inner diameter than the second subspace (19) and is connected to the latter via a step (21) arranged substantially perpendicularly to a longitudinal axis of the first cap part (2).

19. The improvement according to claim 17, characterized in that an inner surface (22) of the second subspace (19) forms a guide surface and the sealing means for the dialyzer flange (4).

20. The improvement according to claim 17, characterized in that the third subspace (20) comprises a frustoconical inner surface (23) which provides a gradual transition between the second subspace (19) and the third subchamber (9).

21. The improvement according to claim 17, characterized in that within the subspaces (18 to 20) concentrically to the connection portion (16) a pot-shaped insert member (24) is fixed having an outer surface (25) which defines with the inner surfaces of the subspaces a free flow passage which creates a flow connection between the open end side (17) of the connection portion (16) and the third subchamber (9) of the first portion (6).

22. The improvement according to claim 21, characterized in that the insert member (24) has an open end side (26) which lies preferably in a plane with the open end side (17).

23. The improvement according to claim 22, characterized in that the insert member (24) comprises a cylindrical boundary wall (27) which is connected at a side opposite the open end side (26) to a closure wall (28).

24. The improvement according to claim 23, characterized in that the closure wall (28) comprises an outer surface (29) directed towards the third subchamber (9).

25. The improvement according to claim 17, characterized in that the third subspace (20) forms a transition between the second subspace (19) and a fourth subspace (41) which is connected via a central connection recess (42) to the third subchamber (9).

26. The improvement according to claim 25, characterized in that the connection recess (42) is defined by an encircling stop wall (43) projecting inwardly to the longitudinal axis.

27. The improvement according to claim 26, characterized in that the stop wall (43) comprises a sealing surface (44) directed towards the third subchamber (9).

28. The improvement according to claim 1, characterized in that the second cap part (3) is pot-shaped and comprises a wall (30) which extends around a longitudinal axis and defines an inner space (31).

29. The improvement according to claim 28, characterized in that the inner space (31) is open at an end side (32) and at an opposite end side is closed by a closure wall (33) arranged substantially perpendicularly to the longitudinal axis.

30. The improvement according to claim 28, characterized in that the wall (30) comprises at least one connection opening (34 or 35) which connects the inner space (31) to an outer wall surface (36).

31. The improvement according to claim 30, characterized in that on the outer wall surface (36) an outwardly directing guide and retaining means (37) is arranged.

32. The improvement according to claim 31, characterized in that the guide and retaining means (37) comprises a resiliently yielding guide ring (38) arranged spaced from the outer wall surface (36) and a stop ring (39) directed outwardly from said guide ring (38).

33. The improvement according to claim 32, characterized in that the guide ring (38) is connected via a collar (40) to the wall (30).

34. The improvement according to claim 1, characterized in that the first cap part (2) is provided with an arresting means (45) which cooperates with a complementary arresting means (46) on the dialyzer flange (4) in the mounted state of the second cap part (2).

35. The improvement according to claim 34, characterized in that the cooperating arresting means and complementary arresting means (45, 46) comprise one of a snap-action, detent, screw and bayonet fastener.

36. The improvement according to claim 34, characterized in that the cooperating arresting means and complementary arresting means (45, 46) are formed as an intactness closure.

37. The improvement according to claim 36, characterized in that the complementary arresting means (46) on the dialyzer flange (4) is formed as nose projection which is provided with a defined intended breakage point.

* * * * *